United States Patent [19]

Corrado et al.

[11] Patent Number: 5,050,778

[45] Date of Patent: Sep. 24, 1991

[54] DRY FLOWABLE MATERIAL DISPENSING AND CONTENTS PRESERVATION AND STERILIZATION APPARATUS

[76] Inventors: Pat Corrado, 497 - 79th St., South, St. Petersburg, Fla. 33707; Stephen Corrado, 9412 Laura Anne Dr., Seminole, Fla. 33542

[21] Appl. No.: 608,479

[22] Filed: Nov. 2, 1990

Related U.S. Application Data

[63] Continuation-in-part of Ser. No. 526,955, May 23, 1990, Pat. No. 4,982,879, which is a continuation of Ser. No. 456,193, Dec. 19, 1989, abandoned, which is a continuation of Ser. No. 204,303, Jun. 9, 1988, abandoned.

[51] Int. Cl.[5] .......... A61L 2/00; B65D 45/00; E05C 1/06

[52] U.S. Cl. .......... 222/152; 220/316; 222/153; 222/355; 222/361; 222/525; 292/144; 422/296; 422/297

[58] Field of Search .......... 292/144, 177; 422/292–310; 220/316; 222/153, 361, 362, 509, 525, 355, 181, 185, 152

[56] References Cited

U.S. PATENT DOCUMENTS

| | | | |
|---|---|---|---|
| 717,448 | 12/1902 | Pease et al. | 422/296 |
| 853,768 | 5/1907 | Caviglia | 222/355 |
| 1,706,051 | 3/1929 | Auchincloss | 220/316 |
| 1,874,833 | 8/1932 | Taylor | 292/144 X |
| 1,936,857 | 2/1933 | Reisdorf | 221/146 |
| 1,988,865 | 1/1935 | Campbell | 222/525 X |
| 2,110,518 | 3/1938 | Becker | 99/236 |
| 2,314,384 | 3/1943 | Berwick et al. | 222/525 X |
| 2,593,770 | 4/1952 | Kollsman | 220/316 X |
| 2,655,290 | 10/1953 | Mansperger | 222/355 X |
| 2,718,239 | 9/1955 | Erbguth | 292/144 X |
| 2,731,978 | 1/1956 | Comer | 222/525 X |
| 2,823,629 | 2/1958 | Wittke | 292/144 X |
| 2,992,761 | 7/1961 | Sommers, Sr. | 222/525 X |
| 3,204,833 | 9/1965 | Weitzner | 222/355 |
| 3,390,822 | 7/1968 | Ballin | 222/355 |
| 3,561,918 | 2/1971 | Ray | 422/300 X |
| 3,739,589 | 6/1973 | Walfe | 292/144 X |
| 3,820,687 | 6/1974 | Brock | 222/52 |
| 4,380,310 | 4/1983 | Schneiter | 222/525 X |
| 4,381,067 | 4/1983 | Catelli | 222/450 |
| 4,505,407 | 3/1985 | Johnson | 222/525 X |
| 4,741,260 | 5/1988 | Bolivar | 220/316 X |
| 4,783,321 | 11/1988 | Spence | 422/297 X |
| 4,915,913 | 4/1990 | Williams et al. | 422/300 X |

FOREIGN PATENT DOCUMENTS

| | | | |
|---|---|---|---|
| 1038865 | 10/1953 | France | 220/316 |

*Primary Examiner*—Kevin P. Shaver
*Attorney, Agent, or Firm*—Kerkam, Stowell, Kondracki & Clarke

[57] ABSTRACT

A pressurizable container has a removable cover. The removable cover has locking elements to maintain the cover sealed to the container when the container is pressurized. The locking device is a piston received in a cylinder, and the cylinder communicates with the interior of the container. When the container is pressurized, the pressure fluid forces the piston and its associated locking bolt into a position such that the bolt passes through a wall of the container and a wall of the removable cover, locking the cover to the container. It is also possible to draw a vacuum on the container when the container is used as a sterilizing device.

6 Claims, 4 Drawing Sheets

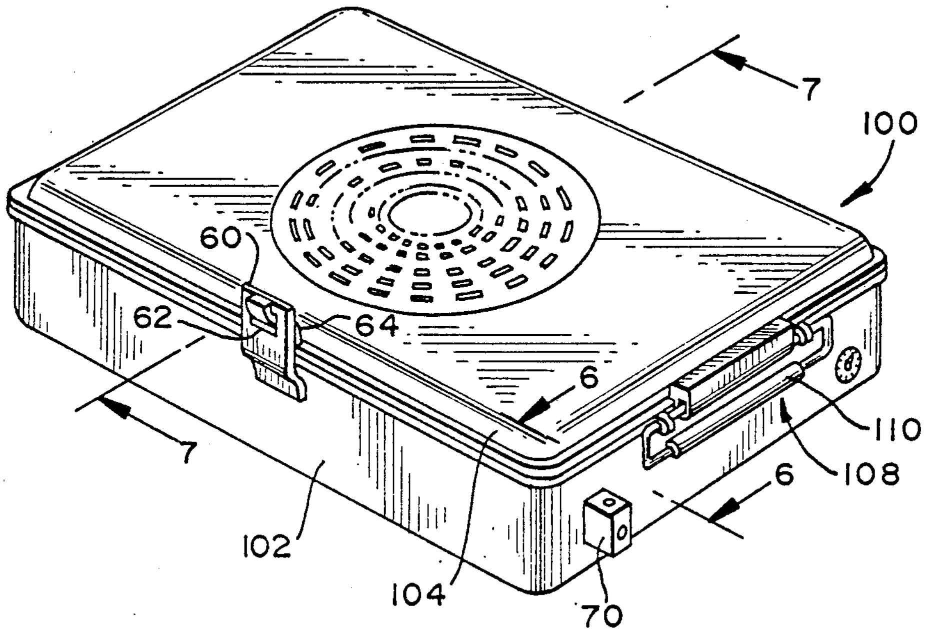
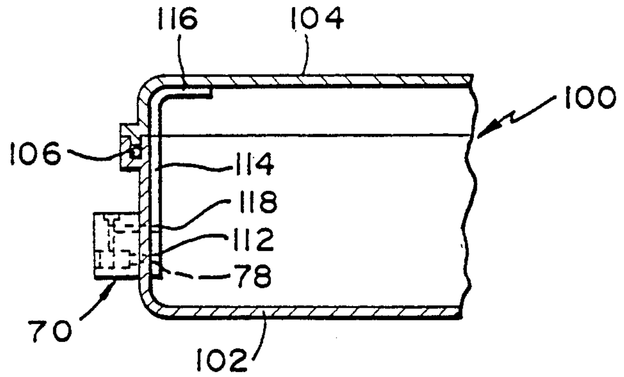
FIG_6
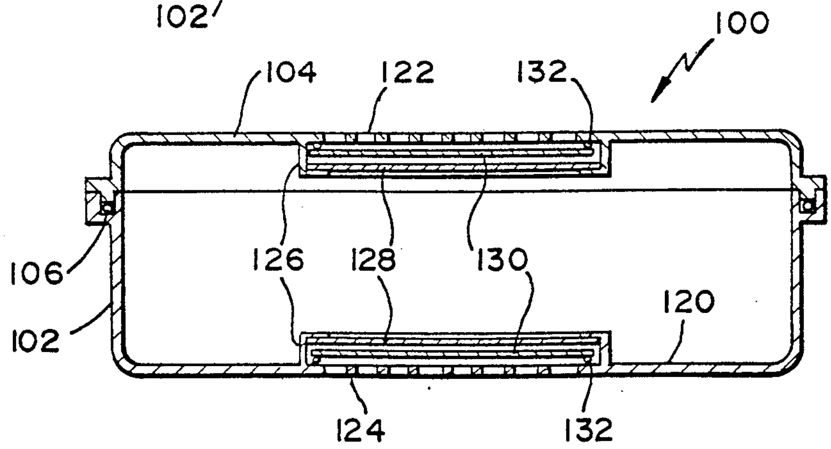
FIG_7

DRY FLOWABLE MATERIAL DISPENSING AND CONTENTS PRESERVATION AND STERILIZATION APPARATUS

CROSS REFERENCE TO RELATED APPLICATIONS

This application is a continuation-in-part of application Ser. No. 526,955, filed May 23, 1990, now U.S. Pat. No. 4,982,879, which is a continuation of application Ser. No. 456,193, filed Dec. 19, 1989, now abandoned, which is a continuation of application Ser. No. 204,303, filed Jun. 9, 1988, now abandoned.

BRIEF SUMMARY OF THE INVENTION

The invention generally relates to a container, the interior of which is maintained above atmospheric pressure by an inert gas such as nitrogen. The container and a container cover have a novel locking mechanism which prevents separation of the cover from the container body as long as the interior of the container is at a pressure above ambience.

In a first aspect of the invention, the container is used as a dispenser for dry, flowable material such as coffee, spices, nuts and sugar, etc., and in a second aspect, the container comprises a sterilization chamber for sterilization and sterile storage of surgical instruments and accessories.

BRIEF DESCRIPTION OF THE SEVERAL VIEWS OF THE DRAWINGS

The invention will be more particularly described in reference to the accompanying drawings wherein:

FIG. 5 is a perspective view of another form of the present invention;

FIG. 6 is a section on line 6—6 of FIG. 5;

FIG. 7 is a section on line 7—7 of FIG. 5; and

DETAILED DESCRIPTION

Figure 2:
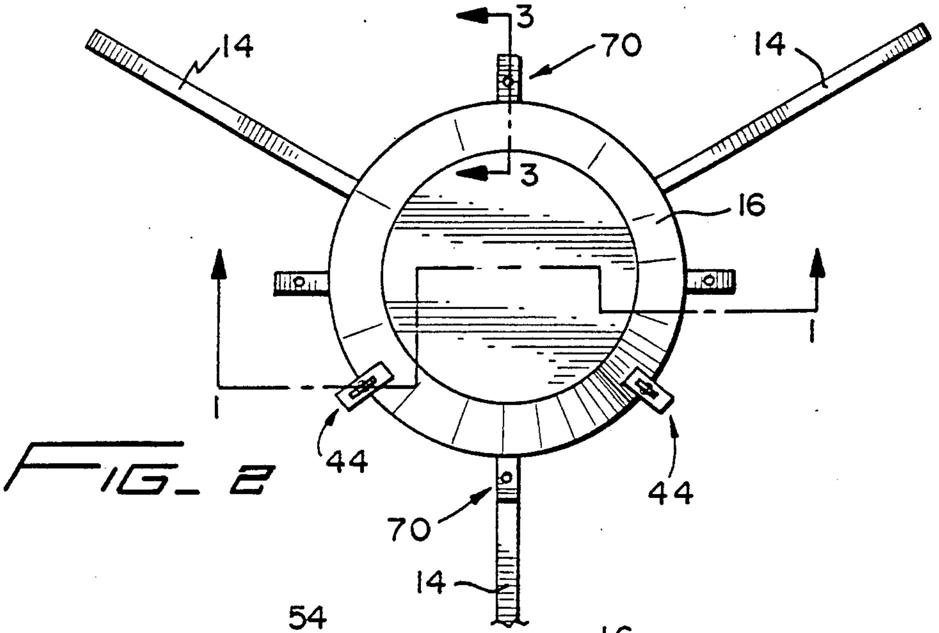
FIG. 2 is a top-plan view of the device shown in FIG. 1.

Referring particularly to FIGS. 1-4, 10 generally designates a container and associated elements for dispensing dry, flowable materials such as spices, coffee, sugar and the like.

The container consists of a base 11 of truncated, conical configuration. The container 11 has secured at its lower end a granular material discharge chute generally designated 12. The container and its discharge chute are supported from a surface by three or more legs, each designated 14.

The assembly also includes a cover for the container 11, designated 16. The cover has welded thereto a number such as four L-shaped brackets 18, which are welded to the cover and are so positioned that a depending portion 20 of each bracket snugly fits within the top portion of the container 11.

Referring again to the discharge chute generally designated 12, the chute receives a covered, hollow cylinder 22, fitted with a pair of O-rings 24, which O-rings pressure-fluid seal the cylinder 22 in the discharged chute 12.

Figure 1:
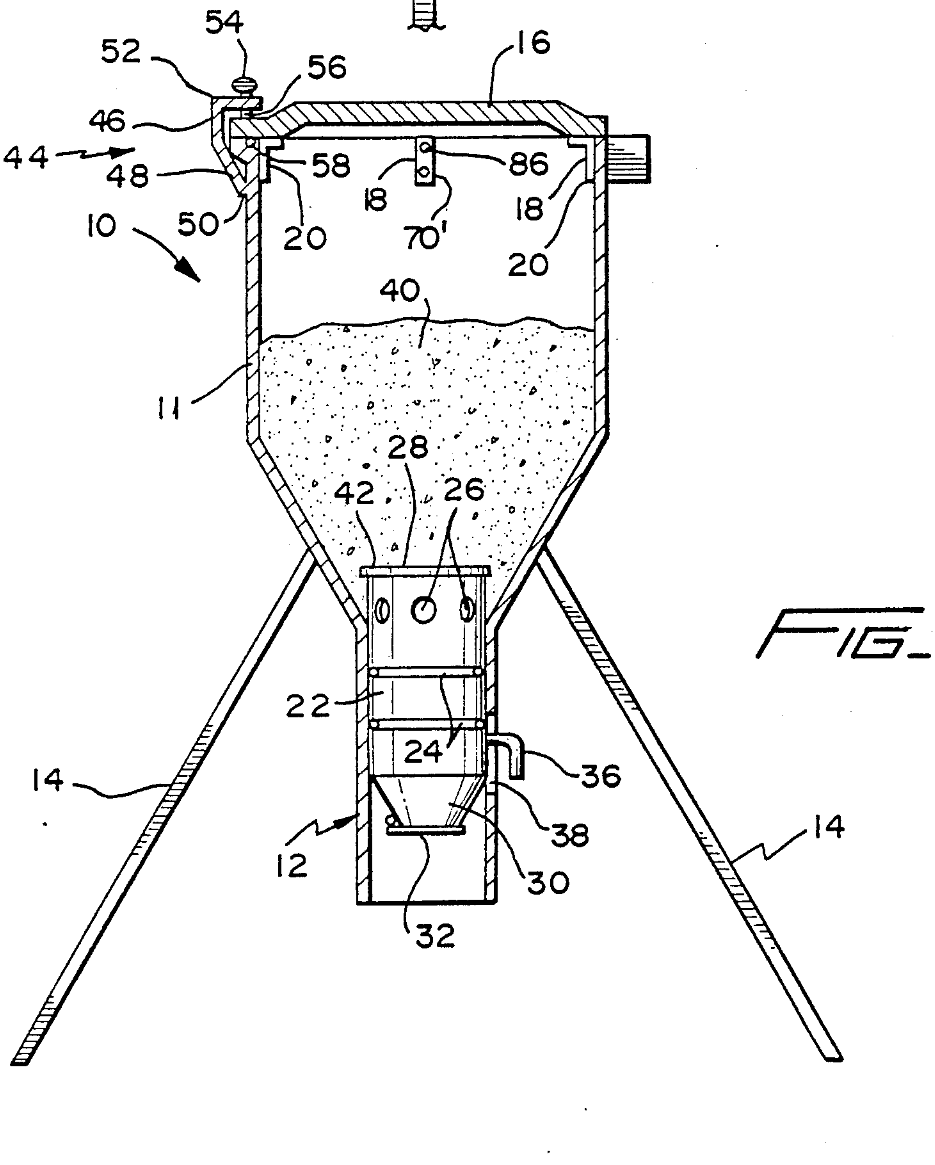
FIG. 1 is a partial, vertical, sectional view through a container for flowable material on line 1—1 of FIG. 2.

At the upper end of the cylinder 22, there are provided a plurality of openings 26 which, when the cylinder is in the position illustrated in FIG. 1, provide communication between the material maintained in the container 11 and the inside of cylinder 12. At the upper end of the cylinder 22 is welded a cover 28 having a diameter slightly larger than the outside diameter of the cylinder 22. At the lower end of the cylinder is a truncated, conical element 30. At the lower end of the truncated element 30 is a door 32 hinged and spring-urged into the closed position.

The cylinder has secured, such as by welding thereto, an operating handle 36 which passes through a slotted opening 38 in one portion of the wall of the discharge chute 12. The slot has a length such that when the operating handle 36 is in its uppermost position, as illustrated in FIG. 1, the openings 26 are in communication with the dry, flowable material generally designated 40 within the container 11. Further, the slot 38 extends downwardly a distance such that when the protruding peripheral edge 42 of the top 28 of the cylinder 22 is in contact with the sloping sidewalls of the container 11, the spring-closed door 32 may be grasped to discharge the contents of the cylinder 22 into a receiving receptacle not shown.

The cover 16 is maintained in a closed position by a plurality such as three or four latch members generally designated 44, comprising a hinge bracket 46 which is pivoted as at 48 to a retainer 50 welded to the outer cylindrical surface of the container 11. The upper, horizontal portion 52 of the bracket 46 is provided with a thumb screw 54 which has a screw-threaded shank which engages as at 56 the cover 16. The member 44 latches the cover 16 to the container 11 and a seal such as O-ring 58 hermetically seals the cover to the container 11.

Figure 3:
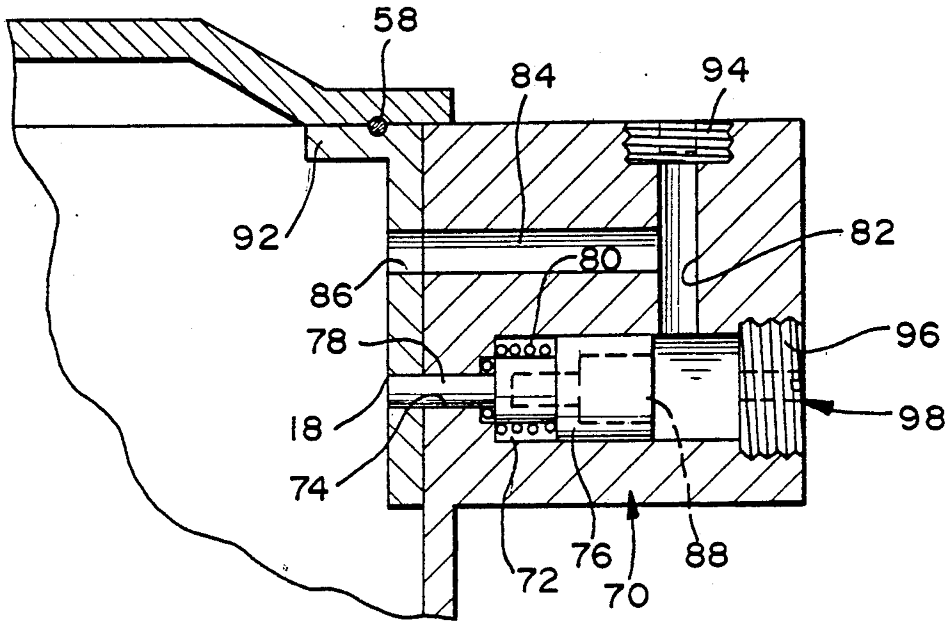
FIG. 3 is a fragmentary, sectional view substantially on line 3—3 of FIG. 2.
Figure 4:
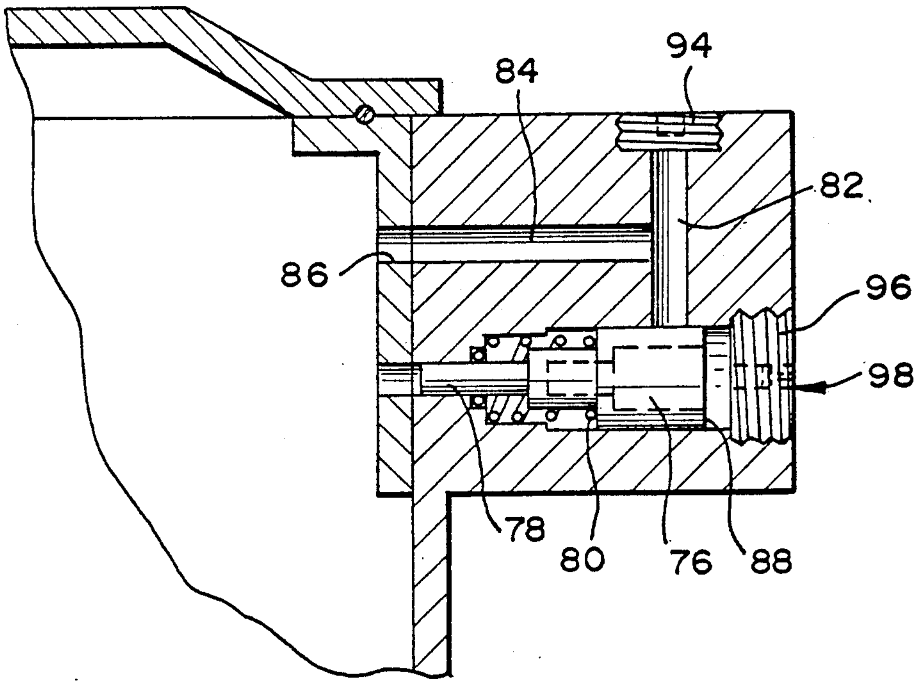
FIG. 4 is a view like FIG. 3 with the locking bolt in the retracted position.

To prevent opening of the container 11 while the container is under pressure, novel pressure-actuated locking means are provided as illustrated in FIGS. 3 and 4. These structures also include the means for pressurizing the container as to be described hereinafter. The pressure-actuated locking mechanism includes a housing 70. The housing 70 has a transverse step bore 72, and a bolt-receiving opening 74, which opening passes through the housing 70, and through each bracket 18. Within the step bore is slidably mounted a piston 76, the inner end of which is of reduced diameter and comprises the bolt 78 which is slidable through the opening 74 in the housing and in the bracket 18. Normally, the piston 76 is urged rearwardly by helical spring 80, as illustrated in FIG. 4.

The housing also includes a bore 82 and a cross-bore 84. The cross-bore 84 communicates with the interior of the container 11 through the opening 86 in each of the brackets 18. The bore 82, which communicates with bore 84, directs pressure fluid within the container 11 to the rear end 88 of the piston 76 whereby the pressure forces the piston inwardly of the housing 70, forcing the bolt 78 into engagement with the opening 74 in each bracket 18. As long as there is pressure in the container 11, the bolt 78 prevents accidental removal of the cover 16 and maintains the seal between the cover, the O-ring 58, and the rim 92 of the cylinder 11. The bore 82 is sealed at its upper end by a plug 94 and the stepped cylinder-bore 72 is closed by a plug 96, which plug is tapped to receive a conventional spring valve such as employed for inflating and deflating automobile tires.

The valve 98 also includes thread means whereby a screw-on cartridge, of conventional form, containing pressurized nitrogen may be attached. Where desired, a large supply of nitrogen may be connected via a pressure base, as in U.S. Pat. No. 4,982,879.

In operation of the structures illustrated in FIGS. 1–4, the material 40 to be dispensed is placed within the cylinder or container 11, and the cover 16 is secured to the container 11 employing the thumb-screws and bracket 54 and 44. When the cover is tightly secured, the cylinder is pressurized to the desired pressure. When pressurizing the container 11, the discharge cylinder 22 may be in the lower or upper positions as the O-ring seals 24 prevent leakage of the pressurizing medium from the container. When it is desired to discharge a quantity of the dry, flowable material 40, the cylinder 22 is moved upwardly by hand-control knob 36 so that the cylinder 22 may be filled via the openings 26. To discharge the contents, the cylinder 22 is moved to its lower position, and the spring-closed door 32 is manually opened to discharge the contents into a suitable receptacle.

Referring now to FIGS. 5–7, another form of the pressurized container is illustrated and generally designated 100, and which illustrates a sterilization container for, e.g., medical instruments and accessories. The container 11 comprises a quadrangular, or the like, base 102 and a cover 104. The cover and the base are shaped to cooperate with an O-ring 106 to provide a gas type seal between the cover 104 and the base 102. The assembly includes a conventional closure element generally designated 108 which includes a handle 110, useful for carrying the container.

At the same end, and at the opposite end, of the container, is mounted a valve-filling mechanism and cover-locking mechanism, as shown in FIGS. 3 and 4, and provided with the same reference characters as those employed in FIGS. 3 and 4. The bolt portion 78 of each pressure-actuated locking device is received in an opening 112 in an L-shaped bracket 114 welded as at 116 to the cover 104. The L-shaped bracket 114 also is provided with an opening 118 which communicates with the piston for actuating the bolt 78 and the interior of the container 100. The lid 104 and the base 120 of the container 100 is provided with means for permitting a sterilizing medium to enter the container through upper and lower grills 122 and 124. Below the grill work 122 and above grill 124, there is mounted a cylindrical flange 126 for each grill 122 and 124. The flange supports a filter paper 128, and between the filter paper and the grill 122 and 124 is a metal plate 130 which has cemented to the outer surface an O-ring 132. In operation, the items desired to be sterilized are placed in the container, and the container is placed in a sterilizing atmosphere or medium which passes through the filter paper 128.

The cover is latched via latch 108 and its counterpart on an opposite wall. When it is desired to maintain the contents in a sterile condition, a pressurizing medium such as nitrogen enters the container via the valve 99 (FIGS. 3 and 4). As the pressure builds up, the safety latch 70 on at least two sides of the container are actuated by pressure fluid, and the metal plates 130 below grill 122 and above grill 124 are urged upwardly and downwardly, respectively, to seal the contents against leakage via the O-ring 132. When it is desired to use the contents of the container 100, the pressure within the container is released via the tire type valve 98, thereby permitting the safety bolts on each of the safety latch means to be withdrawn by their respective coil or helical springs. Then, employing the conventional closure means 108 at each end of the container may be actuated to remove the cover 104 from the container 102.

As a further safety measure, there is provided at least one mechanical latch, as illustrated in FIG. 5. The latch includes a plate 60 having a quadrangular opening 62 therethrough. The plate 60 is welded, or otherwise secured, to a side wall 102 of the container, and a latch member 64 is secured to the top of the container 104. When the keeper 64 is projecting through the opening 62 of latch plate 60, accidental opening of the container is minimized.

Figure 8:
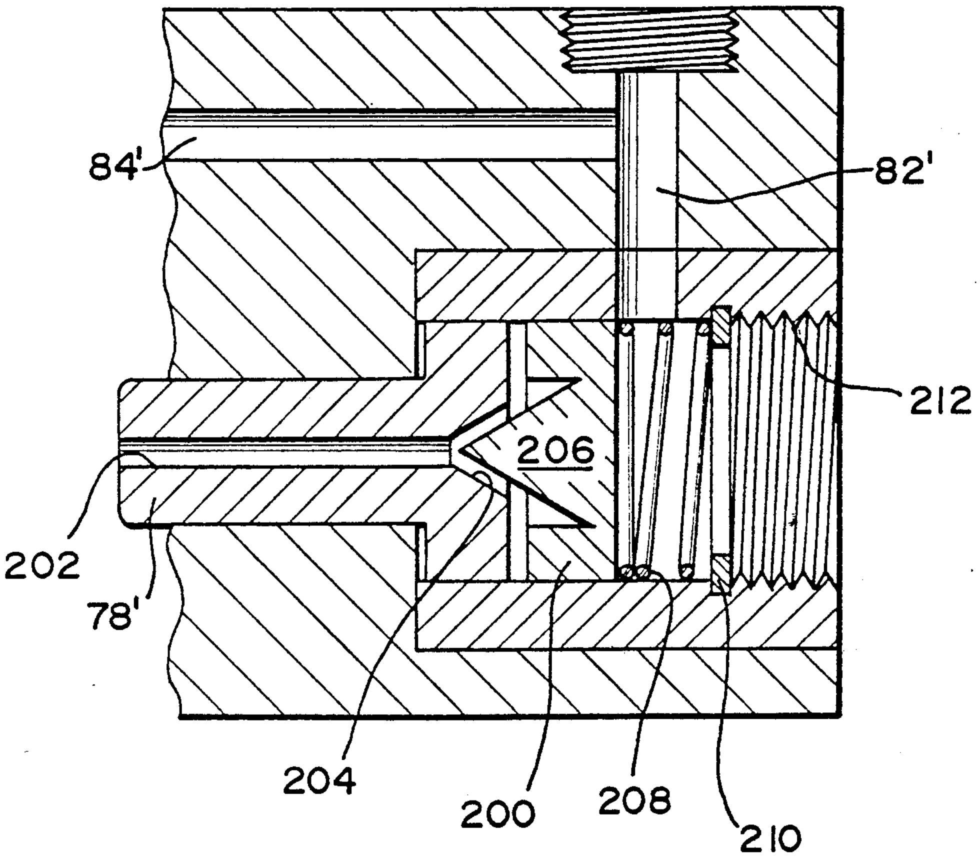
FIG. 8 is a partial sectional view of a modified form of the present invention.

Referring to the modified form of the invention illustrated in FIG. 8, the latching mechanism includes a bolt 78' which is forced by the vacuum valve mechanism 200 to latch the container lid in a locked position when pressure is applied to the mechanism 200.

The bolt is modified to include a passage 202 leading to a conical valve seat 204. The conical valve seat is closed by a conical valve member 206 forming a part of the valve 200. Vacuum applied opens the conical valve seat against the force of spring 208.

The valve 200 is urged toward the valve seat 204 by a spring 208 which abuts at one end against the valve 200 and at the other against a retainer ring 210.

Air pressure is directed to the valve via pressure passage 84' and 82' as in the prior form of the invention.

When it is desired to evacuate the container, a vacuum line is screw threaded onto the threads 212 instead of a pressure connection.

Having described several forms of the present invention, what is claimed is as follows:

1. A container having a removable cover; means for pressurizing the container with an inert gas; means for locking the cover to the container when the container is pressurized, said locking means mounted on the container comprising a lock housing, a stepped cylinder formed in the housing, a stepped piston slidably mounted in the stepped cylinder, a keeper bolt formed at the end of the piston, a first passage at the end of the cylinder through which the keeper bolt can slide; a cooperating bolt-receiving second passage in the container cover; the length of the first and second passages and the keeper bolt is such that when the container is pressurized, the bolt passes into each passage and a third passage at the rearward end of the cylinder connecting the interior of the container with the cylinder and to the means for pressurizing the container, and control means operative with the means for pressurizing the container, said control means including a valve in the housing at the said rearward end of the cylinder.

2. The container as defined in claim 1, including an outlet for contents of the container, said outlet comprising an outlet chute, a hollow cylinder slidably mounted in the outlet; O-rings sealing the hollow cylinder and the wall of the outlet chute, openings at the upper end of the hollow cylinder to communicate with the contents of the container when the hollow cylinder is urged upwardly, and an outlet spring-loaded door at the lower end of the hollow cylinder accessible when the cylinder is moved into a discharge position.

3. The invention defined in claim 1, wherein the container is pressurized with nitrogen.

4. The container as defined in claim 1, further including a pressure fluid outlet valve communicating with the interior of the container and the ambient atmosphere.

5. The invention defined in the claim 4 including a perforated portion on the cover of the container; means for securing a filter paper beneath said perforated section of the container lid; and a flapper valve actuated by pressure within the container to seal the openings covered by said filter paper.

6. The invention defined in claim 1, including means for evacuating the container through a port in said keeper bolt and a cooperating valve mechanism for controlling said means for evacuating the container.

* * * * *